(12) United States Patent
Dekker et al.

(10) Patent No.: US 11,008,269 B2
(45) Date of Patent: May 18, 2021

(54) PROCESS FOR THE PRODUCTION OF ETHYLENE GLYCOL

(71) Applicant: Avantium Knowledge Centre B.V., Amsterdam (NL)

(72) Inventors: Paula Dekker, Amsterdam (NL); Jan Cornelis Van Der Waal, Amsterdam (NL); Gerardus Johannes Maria Gruter, Amsterdam (NL); Jagdeep Singh, Amsterdam (NL); Benjamin McKay, Amsterdam (NL)

(73) Assignee: Avantium Knowledge Centre B.V., Amsterdam (NL)

( * ) Notice: Subject to any disclaimer, the term of this patent is extended or adjusted under 35 U.S.C. 154(b) by 0 days.

(21) Appl. No.: 16/977,758

(22) PCT Filed: Mar. 14, 2019

(86) PCT No.: PCT/EP2019/056518
§ 371 (c)(1),
(2) Date: Sep. 2, 2020

(87) PCT Pub. No.: WO2019/175369
PCT Pub. Date: Sep. 19, 2019

(65) Prior Publication Data
US 2021/0040022 A1    Feb. 11, 2021

(30) Foreign Application Priority Data
Mar. 14, 2018    (NL) ...................................... 2020583

(51) Int. Cl.
*C07C 29/132* (2006.01)
*B01J 23/30* (2006.01)
*C07C 31/20* (2006.01)

(52) U.S. Cl.
CPC ............ *C07C 29/132* (2013.01); *B01J 23/30* (2013.01); *C07C 31/202* (2013.01)

(58) Field of Classification Search
CPC ....... C07C 29/132; C07C 31/202; B01J 23/30
See application file for complete search history.

(56) References Cited
U.S. PATENT DOCUMENTS
2018/0362424 A1* 12/2018 Chewter ............... C07C 29/132

FOREIGN PATENT DOCUMENTS

| | | |
|---|---|---|
| CN | 102643165 B | 7/2014 |
| CN | 106868305 A | 6/2017 |
| WO | 2017097847 A1 | 6/2017 |

OTHER PUBLICATIONS

International Search Report and Written Opinion dated Jun. 21, 2019 for PCT/EP2019/056518.

* cited by examiner

*Primary Examiner* — Jafar F Parsa
(74) *Attorney, Agent, or Firm* — Suiter Swantz pc llo (57) ABSTRACT

A process for the production of ethylene glycol including the steps of:
(i) providing, to a first reactor, a carbohydrate source, a solvent, hydrogen, a first heterogeneous catalyst, which first heterogeneous catalyst contains one or more transition metals from groups 8, 9 and 10 of the Periodic Table of the Elements, and a homogeneous catalyst, which homogeneous catalyst contains tungsten;
(ii) reacting, in the first reactor, at a temperature in the range from equal to or more than 170° C. to equal to or less than 270° C., at least a portion of the carbohydrate source in the presence of the hydrogen, the solvent, the first heterogeneous catalyst and the homogeneous catalyst;
(iii) removing, from the first reactor, a first reactor product stream and separating from such first reactor product stream at least:
one ethylene glycol rich fraction; and
one sorbitol-rich fraction containing concentrated homogeneous catalyst;
(iv) providing, to a second reactor, hydrogen and at least part of the sorbitol-rich fraction, containing concentrated homogeneous catalyst;
(v) reacting, in the second reactor, at a temperature in the range from equal to or more than 200° C. to equal to or less than 300° C., at least a part of the sorbitol-rich fraction, containing concentrated homogeneous catalyst, in the presence of the hydrogen, a second heterogeneous catalyst, which second heterogeneous catalyst contains one or more transition metals from groups 8, 9 and 10 of the Periodic Table of the Elements;
(vi) removing, from the second reactor, a second reactor product stream.

15 Claims, 1 Drawing Sheet

PROCESS FOR THE PRODUCTION OF ETHYLENE GLYCOL

FIELD OF THE INVENTION

The present invention relates to a process for the production of ethylene glycol.

BACKGROUND TO THE INVENTION

Alkylene glycols, such as ethylene glycol, are bulk chemicals that can be used in a wide variety of applications. They can be used as monomer in the preparation of polyesters, such as poly(ethylene terephthalate), poly(ethylene naphthenate) or poly(ethylene furandicarboxylate), but ethylene glycol can also be used for example in heat transfer media and anti-freeze compositions.

Recently, increased efforts are being made to produce alkylene glycols from sustainable resources, such as carbohydrates. By enabling the preparation of alkylene glycols, such as ethylene glycol, from sustainable resources, the dependence of fossil fuel resources is advantageously reduced.

CN102643165 describes a method for producing ethylene glycol and 1,2-propylene glycol through continuous hydrocracking of sugars. The method is carried out in a reactor using a catalytically active tungsten species. The liquid reactor effluent is separated into two parts. One part of the liquid reactor effluent is fed to a distillation system and another part of the liquid reactor effluent is returned directly to the reactor for diluting the reaction liquid. In the distillation system, polyol heavies and unreacted saccharide are obtained that are returned to the reactor for further hydrocracking. In this manner, dissolved tungsten components in the heavies are recovered and recycled to the reaction.

Also WO2016/114658 describes a process for preparing ethylene glycol from a carbohydrate source. The carbohydrate source is reacted with hydrogen in the presence of a diluent and a catalyst system comprising a tungsten compound and at least one hydrogenolysis metal selected from the groups 8, 9 or 10 of the Periodic Table of the Elements. WO2016/114658 indicates that higher polyols, such as glycerol, erythritol, or sorbitol, tend to be produced as by-products in a process for preparing ethylene glycol from carbohydrates. Possibly a polyol, e.g. glycerol, xylytol, sorbitol or erythritol, can be added to the diluent. They can also be used as an entraining agent for butylene glycol and subsequently recycled to the process. The process can be operated in a continuous operation mode: wherein the feedstock comprises at least a diluent (comprising an alkylene glycol) and a carbohydrate source; and wherein such feedstock is passed through a plug flow reactor in the presence of hydrogen and also in the presence of a catalyst system.

Although higher polyols, such as sorbitol, can be recycled as described in WO2016/114658, a substantial recycle of such higher polyols is not desirable. At the reactor conditions for converting a carbohydrate source, higher polyols such as sorbitol cannot be completely converted. As a result the concentration of such higher polyols would slowly build up, making the process less suitable for continuous operation.

WO 2015028398 describes a process for the preparation of ethylene glycol and 1,2-propylene glycol from starting material comprising one or more saccharides, wherein the process comprises the steps of i) providing the starting material and hydrogen to a first reactor, which first reactor operates with mixing; ii) reacting said starting material and hydrogen in the first reactor in the presence of solvent and a catalyst system; iii) continuously removing a first reactor product stream from the first reactor; iv) supplying at least a portion of the first reactor product stream to a second reactor, which reactor operates essentially in a plug flow manner; and v) further reacting the first reactor product stream with hydrogen in the presence of a solvent and optionally a catalyst system in the second reactor. The catalyst system can comprise one or more materials selected from transition metals from groups 8, 9 or 10 or compounds thereof and one or more materials selected from tungsten, molybdenum and compounds and complexes thereof. In one embodiment, a homogeneous catalyst system is used in the first reactor, that may remain in the first reactor product stream and is supplied to the second reactor within that stream.

WO 2015028398 wishes to obtain full conversion of the starting material and/or any intermediates and wishes to reduce the formation of by-products. The reduction of formation of by-products is, however, not illustrated by the examples. On the contrary, as illustrated by the examples of WO 2015028398, whilst in examples 2 and 3 the formation of desired product mono-ethylene glycol increases with tens of percent, the formation of 1,2 butanediol by-product increases with hundreds of percent. The formation of higher polyol by-products such as glycerol, erythritol, or sorbitol was not determined, but can be expected to have also increased under these circumstances.

It would be an advancement in the art to provide an improved process for the preparation of ethylene glycol, that allows one to avoid build-up of higher polyols (also referred to as heavy polyols), such as sorbitol in the process. It would further be an advancement in the art if the build-up of such heavy polyols could be prevented in an economically attractive manner.

SUMMARY OF THE INVENTION

Such a process has been obtained with the process according to the invention. Accordingly the present invention provides a process for the production of ethylene glycol including the steps of:

(i) providing, to a first reactor, a carbohydrate source, a solvent, hydrogen, a first heterogeneous catalyst, which first heterogeneous catalyst contains one or more transition metals from groups 8, 9 and 10 of the Periodic Table of the Elements, and a homogeneous catalyst, which homogeneous catalyst contains tungsten;

(ii) reacting, in the first reactor, at a temperature in the range from equal to or more than 170° C. to equal to or less than 270° C., at least a portion of the carbohydrate source in the presence of the hydrogen, the solvent, the first heterogeneous catalyst and the homogeneous catalyst;

(iii) removing, from the first reactor, a first reactor product stream and separating from such first reactor product stream at least:
  one ethylene glycol rich fraction; and
  one sorbitol-rich fraction containing concentrated homogeneous catalyst;

(iv) providing, to a second reactor, hydrogen and at least part of the sorbitol-rich fraction, containing concentrated homogeneous catalyst;

(v) reacting, in the second reactor, at a temperature in the range from equal to or more than 200° C. to equal to or less than 300° C., at least a part of the sorbitol-rich fraction, containing concentrated homogeneous catalyst, in the presence of the hydrogen, a second heterogeneous catalyst, which second heterogeneous catalyst contains one or more transition metals from groups 8, 9 and 10 of the Periodic Table of the Elements;

(vi) removing, from the second reactor, a second reactor product stream.

Step (vi) may further advantageously comprise the optional recycling at least a portion of the second reactor product stream to the first reactor.

As indicated by WO2016114658, higher polyols, such as glycerol, erythritol, or sorbitol, tend to be produced as by-products in the first reactor. These higher polyols have high boiling points (i.e. boiling points above 250° C. at atmospheric pressure of 0.1 Megapascal) and are herein also referred to as "heavy polyols". By a polyol is herein understood an organic compound comprising multiple, suitably three or more, hydroxyl groups. A heavy polyol by-product of specific interest is sorbitol.

As explained above, mere recycling of such heavy polyols would lead to a slow build-up in concentration of the heavy polyols in a reactor product stream, making a process less suitable for continuous operation. As illustrated in WO 2015028398, merely further reacting a reactor product stream from a first reactor in a further second reactor also does not resolve the problem.

The high solubility of the homogeneous catalyst in the heavy polyols further makes it difficult to separate such homogenous catalyst from a reactor product stream by precipitation and/or filtration. The removal of the heavy polyols by vacuum distillation has also been found to be challenging.

By separating the heavy polyols and converting such heavy polyols into lower boiling products in a separate second reactor, a stream containing homogeneous catalyst dissolved in a mixture containing alkylene glycols, other diols and/or other polyols can be obtained that is very suitable for recycling to the first reactor. The homogeneous catalyst can also be more easily separated from such mixture by evaporation, distillation, precipitation and/or filtration.

Inventors have now surprisingly found that the conversion of the heavy polyols is possible in a second reactor, if in such second reactor a catalyst system is used with higher concentrations of homogeneous catalyst than present in the first reactor.

Advantageously, with the process according to the invention, sorbitol by-product formed in the first reactor can be concentrated in a sorbitol-rich fraction, containing also concentrated homogeneous catalyst. Subsequently such sorbitol-rich fraction can advantageously be forwarded together with the concentrated homogeneous catalyst to the second reactor, where the sorbitol can be at least partially converted into lower boiling products.

BRIEF DESCRIPTION OF THE DRAWINGS

The invention is illustrated by the following figures.

DETAILED DESCRIPTION OF THE INVENTION

Step (i) comprises providing, to a first reactor, a carbohydrate source, a solvent, hydrogen, a first heterogeneous catalyst, which first heterogeneous catalyst contains one or more transition metals from groups 8, 9 and 10 of the Periodic Table of the Elements, and a homogeneous catalyst, which homogeneous catalyst contains tungsten.

By a carbohydrate source is herein understood a source of carbohydrates. The carbohydrate source can be selected from a variety of sources. Preferably, the carbohydrate source comprises one or more carbohydrates chosen from the group consisting of polysaccharides, oligosaccharides, disaccharides, monosaccharides and mixtures thereof.

Suitable examples may include, preferably sustainable, sources of carbohydrates such as cellulose, hemicellulose, starch, sugars, such as sucrose, mannose, arabinose, fructose, glucose and mixtures thereof. Carbohydrate sources that contain the above carbohydrates may include dextrose syrups, maltose syrups, sucrose syrups, glucose syrups, crystalline sucrose, crystalline glucose, wheat starch, corn starch, potato starch, cassava starch, and other carbohydrate containing streams, for example paper pulp streams, wood waste, paper waste, agricultural waste, cellulosic residues recovered from municipal waste, paper, cardboard, sugar cane, sugar beet, wheat, rye, barley, corn, rice, potatoes, cassava, other agricultural crops and combinations thereof. These streams may require pre-treatment to extract the carbohydrates (for example wet milling in the case or corn) or to remove components that interfere with the current process such as basic fillers (for example the removal of calcium carbonate in waste paper). In this way the process according to the invention can use natural sources, but can also be used to upgrade and usefully re-use waste streams. Preferably, the carbohydrates in the carbohydrate source are chosen from the group consisting of cellulose, hemicellulose, starch, glucose, sucrose, glucose-oligomers and combinations thereof. Since cellulose presents difficulties that are absent in other carbohydrate sources, the carbohydrate source is most preferably selected from the group consisting of starch, hemicelluloses and hemicellulosic sugars, glucose and mixtures thereof. Most preferably the carbohydrate source comprises or consists of glucose, fructose, sucrose or a combination thereof.

Suitably, the carbohydrate source can be provided to the first reactor together with at least part of a solvent. More preferably, the carbohydrate source is partially or wholly dissolved in such a solvent. Preferences for such solvent are provided below. The solvent can for example be an aqueous medium, an organic medium including alkylene glycols, or a mixture containing water, diols and/or other polyols. Many carbohydrates are soluble in water or a mixture containing water, diols and/or other polyols. The carbohydrate source can also be provided to the first reactor in the form of a slurry. Examples of such slurries include aqueous mixtures of water and hemicellulose, hemicellulosic sugars, glucose and/or starch.

The present process advantageously allows for the provision to the first reactor of a very concentrated feed stream containing the carbohydrate source. When employing such a concentrated feed stream the process economics benefit. Such a feed stream may suitably comprise the carbohydrate source and a solvent, for example water and/or diols and/or other polyols.

Preferably the carbohydrate source is provided to the first reactor by a feed stream containing the carbohydrate source and a solvent, wherein such feed stream contains in the range from equal to or more than 1.0 wt. % (weight percent), preferably equal to or more than 10.0 wt. %, and more preferably equal to or more than 20.0 wt. % to equal to or less than 90.0 wt. %, preferably equal to or less than 70.0 wt. % and more preferably equal to or less than 50.0 wt. % carbohydrate source, based on the total weight of the carbohydrate source and solvent. A feed stream containing carbohydrate source within this concentration range can suitably be easily transported. The feed stream can also consist of only (100 wt. %) carbohydrate source. For practical purposes the carbohydrate source can be provided to the first reactor by a feed stream containing the carbohydrate source and a solvent, wherein such feed stream contains in the range from equal to or more than 2.0 wt. %, more preferably equal to or more than 10.0 wt. %, to equal to or less than 50.0 wt. %, more preferably to equal to or less than 30.0 wt. % of carbohydrate source, based on the total weight of the carbohydrate source and solvent. Most preferably a feed stream containing or consisting of carbohydrate source and solvent is provided to the first reactor, wherein such feed stream contains in the range of equal to or more than 20.0 wt. % to equal to or less than 50.0 wt, %, more preferably equal to or less than 30.0 wt. % of carbohydrate source, based on the total weight of the carbohydrate source and solvent. It is believed that such a feedstream containing equal to or more than 20.0 wt. % of carbohydrate source can make the process economically more attractive. Such solvent may comprise any of the solvents mentioned below, but is preferably water. Most preferably the carbohydrate source is provided to the first reactor by a feed stream containing the carbohydrate source and water, wherein such feed stream contains in the range from equal to or more than 2.0 wt. % to equal to or less than 30.0 wt. % of carbohydrate source, based on the total weight of the carbohydrate source and water.

Preferably the carbohydrate source is continuously or periodically added to the first reactor. Preferably the carbohydrate source is provided to the first reactor under a blanket of inert gas, such as nitrogen.

Preferably part of the solvent is provided by at least a portion of the second reactor product stream, being recycled from step (vi). Such at least portion of the second reactor product stream preferably comprises homogeneous catalyst dissolved in solvent. Such solvent can suitably comprise products of the conversion of the heavy polyols, for example alkylene glycols and/or other diols. As explained below, these alkylene glycols and/or other diols can be very suitable solvents.

Solvent can be supplied as part of a feed stream comprising carbohydrate source, as described above. It is also possible for the solvent to be provided to the first reactor separately or independently from the carbohydrate source and/or the second reactor product stream.

Preferably a feed stream is used containing the carbohydrate source and solvent. The concentration of carbohydrate source in such a feed stream may suitably be adjusted such that sufficient solvent is provided to the first reactor.

Water can be a very suitable solvent as most carbohydrates are soluble in water. Such water may optionally be mixed with organic solvents that have a beneficial effect on the solubility of the any of the reactants or have any other advantage.

The solvent is hence preferably selected from the group consisting of water and organic solvents, such as, dials and/or other polyols, and mixtures thereof. Suitably the solvent can be a mixture of water and, optionally, one or more of the above-mentioned organic solvents. Alkanols are preferred as organic solvent. Such alkanols can be mono-alkanols, preferably water-miscible mono-alkanols, such as methanol, ethanol, propanol, butanol and mixtures thereof. For the process according to the invention, such light mono-alkanols are, however, less preferred. The alkanol can also be a water-miscible diol or other polyol, e.g. ethylene glycol, propylene glycol, butylene glycol, glycerol, xylytol, sorbitol or erythritol. By a diol is herein understood an organic compound comprising two hydroxyl groups. Preferably the solvent comprises an alkylene glycol. Examples of preferred alkylene glycols include ethylene glycol, propylene glycol, butylene glycol and mixtures thereof. The use of alkylene glycol is especially advantageous as it has been found that diols and/or polyols, including alkylene glycols, facilitate the dissolution of tungsten or a tungsten compound into the solvent, thereby promoting the catalytic activity of the tungsten or tungsten compound. It has further been found that the selectivity of the reaction to alkylene glycols is enhanced by the use of alkylene glycol as component in the solvent. Without wishing to be bound by any theory, it is believed that tungsten forms complexes with alkylene glycol whereby the conversion to by-products is reduced. Moreover, the use of an alkylene glycol as solvent does not involve the introduction of an extraneous reagent into the reaction mixture, which represents a further advantage. Preferably the solvent comprises or consists of water, one or more alkylene glycols, one or more alkanols, optionally one or more heavy polyols, or a mixture of two or more thereof. Most preferably the solvent comprises a mixture of water, one or more alkylene glycols and optionally one or more heavy polyols.

Preferably the solvent is continuously or periodically added to the first reactor. At the same time a portion of the solvent may be continuously or periodically withdrawn from the first reactor.

The hydrogen can be supplied as substantially pure hydrogen. Alternatively, the hydrogen may be supplied in the form of a mixture of hydrogen and an inert gas. The inert gas can suitably be selected from nitrogen, argon, helium, neon and mixtures thereof. The volume ratio of hydrogen to the inert gas may vary between wide ranges. Suitably, the volume ratio is not very low, since the reaction proceeds well when the hydrogen partial pressure is sufficiently high. Accordingly, the volume ratio between hydrogen and the inert gas may be from 1:1 to 1:0.01. More preferably, only hydrogen is used as gas in the process according to the invention.

The total pressure during the reaction comprises the vapour pressure of the solvent and the reactants at the temperature and pressure applied in addition to the partial pressure of the hydrogen and, if present, the partial pressure of any inert gas. Preferences for the total pressure are provided below.

Hydrogen can suitably be provided via a dip tube, for example a dip tube close to an agitator, or via a distributor, for example a sparger, to the first reactor. Via such dip tube or distributor and optionally via one or more stirring mechanisms, hydrogen can be dissolved in the reaction mixture. Preferably the hydrogen is continuously or periodically added to the first reactor.

In addition to the carbohydrate source, the solvent and the hydrogen, a homogeneous catalyst, which homogeneous catalyst contains tungsten, and a heterogeneous catalyst, which heterogeneous catalyst comprises one or more transition metals from groups 8, 9 and 10 of the Periodic Table of the Elements, are provided to the first reactor.

The homogeneous catalyst and heterogeneous catalyst are together herein also referred as the catalyst system.

The homogeneous catalyst is herein also referred to as tungsten-comprising homogenous catalyst.

The tungsten can be present as elemental tungsten or as a tungsten compound. Such tungsten compound can for example be tungstic acid or a tungstate salt. The homogeneous catalyst can therefore suitably contain one or more tungsten compounds. The tungsten or tungsten compound(s) can suitably be dissolved in the reaction mixture. Preferably, the tungsten has an oxidation state of at least +2. More preferably the tungsten has an oxidation state of +5 or +6. When dissolved in the reaction mixture the dissolved tungsten or dissolved tungsten compound may form complexes with (other) components of the solvent and/or reaction mixture.

The homogeneous catalyst provided to the first reactor can be freshly made homogeneous catalyst or recycled homogeneous catalyst originating from for example the second reactor product stream. Freshly made homogeneous catalyst is herein also referred to as "virgin" homogeneous catalyst. Such virgin homogeneous catalyst is preferably selected from the group consisting of tungstic acid ($H_2WO_4$) and tungstate compounds such as tungstic salts, for example comprising at least one Group 1 or 2 element, for example sodium tungstate ($Na_2WO_4$) or potassium tungstate ($K_2WO_4$) or for example comprising ammonium tungstate, and combinations of one or more of these.

Recycled homogeneous catalyst can be simply referred to as "recycled" homogeneous catalyst. Preferably the homogeneous catalyst provided to the first reactor in step (i) contains recycled homogeneous catalyst or a combination of virgin homogeneous catalyst and recycled homogeneous catalyst. The homogeneous catalyst provided to the reactor in the current invention can for example contain or consist of recycled tungsten species recovered, directly or indirectly (for example via distillation) from the effluent of a reactor.

Any recycled homogeneous catalyst may contain tungsten as a complex with components from the solvent in which such homogeneous catalyst may be dissolved. The recycled homogeneous catalyst may therefore suitably comprise tungsten in a form derived from a precursor tungsten compound as originally provided.

Preferably the homogeneous catalyst contains a tungsten compound or tungsten derived from a tungsten compound, wherein such tungsten compound is selected from the group consisting of tungstic acid ($H_2WO_4$), tungsten bronze (present as $H_xWO_3$ or $M_xWO_3$, wherein x is a variable smaller than 1 (<1) and M is a metal, for example an alkali or alkali earth metal), ammonium tungstate, ammonium metatungstate, ammonium paratungstate, tungstate compounds comprising at least one Group 1 or 2 element, metatungstate compounds comprising at least one Group 1 or 2 element, paratungstate compounds comprising at least one Group 1 or 2 element, tungsten oxide ($WO_3$), heteropoly compounds of tungsten, and combinations thereof. Tungstic acid ($H_2WO_4$), tungsten bronze ($H_xWO_3$) and tungstate compounds comprising at least one Group 1 or 2 element, for example sodium tungstate ($Na_2WO_4$) or potassium tungstate ($K_2WO_4$), are preferred. Most preferably the homogeneous catalyst contains a tungsten compound or tungsten derived from a tungsten compound, wherein such tungsten compound is sodium tungstate and/or tungstic acid and/or tungsten bronze.

It has been found that the catalytic activity of the tungsten or tungsten compound advantageously increases if the tungsten or suitably the tungsten compound is dissolved. Preferably the homogeneous catalyst is continuously or periodically added to the first reactor. Preferably such homogeneous catalyst that is continuously or periodically added contains tungsten that has an oxidation state of at least +2. Preferably the homogeneous catalyst is chosen from the group consisting of tungstic acid ($H_2WO_4$), tungsten bronze ($H_xWO_3$), sodium tungstate, a dissolved tungstate ion, a dissolved metatungstate ion and a dissolved paratungstate ion.

As the tungsten can be present in so many forms, the tungsten compounds are herein also referred to as tungsten species. By a tungsten species is herein understood any compound comprising or consisting of tungsten element in any kind of form or oxidation state.

Preferably the homogeneous catalyst is dissolved in a solvent. Such solvent can be any solvent as described above. The composition of the solvent may vary during the process. Whilst the reaction is carried out in the first reactor, the solvent may be formed by the reaction mixture itself.

The amount of tungsten that is provided to the first reactor is preferably such that the concentration thereof in the reactor is maintained substantially constant. By substantially constant is herein understood that the difference between the highest and the lowest amounts of tungsten does not vary more than 10% from the average amount of tungsten in the reactor. Preferably the process according to the invention is a continuous or semi-continuous process. Preferably the tungsten compound is continuously or periodically added to the first reactor. At the same time a portion of the tungsten compound may be continuously or periodically withdrawn from the first reactor, suitably via the first reactor product stream. Whereas it is feasible to add tungsten periodically, it is preferred to provide for a continuous addition of tungsten to the first reactor. More preferably the tungsten compound is added to the reactor as a solution of tungsten compound in the solvent.

Preferably the concentration of tungsten compound in the reaction mixture during the reaction ranges from equal to or more than 0.01 wt. % (corresponding to 100 parts per million by weight (ppmw)) to equal to or less than 1.0 wt. % of tungsten (calculated as tungsten metal), based on the total weight of the reaction mixture. More preferably the concentration of tungsten compound in the reaction mixture during the reaction ranges from equal to or more than 0.01 wt. % (corresponding to 100 parts per million by weight (ppmw)), preferably equal to or more than 0.05 wt. % to equal to or less than 0.5 wt. % of tungsten (calculated as tungsten metal) based on the total weight of the reaction mixture.

The first heterogeneous catalyst and the second heterogeneous catalyst each independently comprise one or more transition metals from groups 8, 9 and 10 of the Periodic Table of the Elements. As illustrated in WO2016/114658 the transition metal(s) can be selected from a wide range of transition metals. Preferably the one or more transition metal(s) is/are selected from the group consisting of Cu, Fe, Ni, Co, Pt, Pd, Ru, Rh, Ir, Os and combinations thereof. More preferably the one or more transition metal(s) is/are selected from the group consisting of Ni, Pd, Pt, Ru, Rh, Ir and combinations thereof. Most preferred are nickel, ruthenium and combinations thereof. It has been found that these metals give good yields. The transition metal can suitably be present in its metallic form or as its hydride or oxide or as another compound. It is also possible for the transition metal to be present in a partly tungstated form. By a partly tungstated transition metal is herein understood a transition metal that is partly covered with deposited tungsten species.

The first heterogeneous catalyst, respectively the second heterogeneous catalyst, each independently preferably comprise one or more transition metals from groups 8, 9 and 10 of the Periodic Table of the Elements, supported on a carrier. The carrier may be selected from a wide range of known carrier materials. Suitable carriers include activated carbon (also referred to as "active carbon"), silica, zirconia, alumina, silica-alumina, titania, niobia, iron oxide, tin oxide, zinc oxide, silica-zirconia, zeolitic aluminosilicates, titanosilicates, magnesia, silicon carbide, clays and combinations thereof. By activated carbon is herein understood an amorphous form of carbon with a surface area of at least 800 m$^2$/g. Such activated carbon suitably has a porous structure. Most preferred carriers are activated carbon, silica, silica-alumina and alumina. Even more preferably, the catalyst comprises ruthenium and/or nickel as the transition metal and activated carbon as the carrier. Most preferably the first heterogeneous catalyst contains ruthenium and/or nickel supported on activated carbon and/or the second heterogeneous catalyst contains ruthenium and/or nickel supported on activated carbon. Most preferably the heterogeneous catalyst contains ruthenium, preferably supported on activated carbon.

As explained in more detail below, the first heterogeneous catalyst and/or second heterogeneous catalyst can for example be present as an emulsion, a slurry or as a fixed bed. Preferably the first heterogeneous catalyst and/or second heterogeneous catalyst, each independently, comprise in the range from equal to or more than 1.0 wt. % to equal to or less than 50.0 wt. % of transition metal, more preferably equal to or more than 2.0 wt. %, still more preferably equal to or more than 5.0 wt. %, to equal to or less than 50.0 wt. %, more preferably equal to or less than 20.0 wt. % transition metal, on the basis of the total weight of transition metal and carrier. If a feed stream to the first reactor is used containing in the range of equal to or more than 20.0 wt. % of carbohydrate source, based on the total weight of the carbohydrate source and solvent, preferably a first heterogeneous catalyst is used comprising in the range of equal to or more than 5.0 wt. %, more preferably equal to or more than 10.0 wt. %, to equal to or less than 50.0 wt. %, more preferably equal to or less than 20.0 wt. % of transition metal, on the basis of the total weight of transition metal and carrier, is used. It is believed that such a higher loading of transition metal can advantageously assist to convert a feedstream with a higher concentration of carbohydrate source.

It is possible for the first heterogeneous catalyst to comprise more than one metal. Suitably, the first heterogeneous catalyst can comprise at least one noble metal, selected from the group consisting of Pd, Pt, Ru, Rh and Ir, in combination with a transition metal selected from the group of transition metals from groups 8, 9 or 10 of the Periodic Table of the Elements. The first heterogeneous catalyst can for example comprise a combination of metals, for example Ni/Ir, Ni/Pt, Ni/Pd, Ni/Ru, Ru/Ir, Ru/Pt or Ru/Pd.

Furthermore, as explained in more detail below, during reaction tungsten species may become deposited onto the first heterogeneous catalyst and/or second heterogeneous catalyst. Therefore at least a portion of the first heterogeneous catalyst and/or at least a portion of the second heterogeneous catalyst can contain tungsten in addition to the one or more transition metals from groups 8, 9 and 10 of the Periodic Table of the Elements.

Preferably the process according to the invention is a continuous or semi-continuous process. Preferably a slurry of first heterogeneous catalyst, for example together with solvent, is periodically or continuously added to the first reactor.

During step (ii) at least part of the transition metal may become tungstated. By tungstated is herein understood that such transition metal becomes covered with deposited tungsten species. Any partly or wholly tungstated heterogeneous catalyst may be partly rejuvenated and recycled. Therefore, the first heterogeneous catalyst provided to the first reactor may or may not comprise any tungstated transition metal.

Preferably such a slurry of first heterogeneous catalyst comprises in the range from equal to or more than 5 wt. % to equal to or less than 90 wt. %, more preferably equal to or less than 70 wt. %, most preferably equal to or less than 50 wt. % of heterogeneous catalyst, based on the total weight of such slurry. Preferably such a slurry is a slurry of heterogeneous catalyst in water and/or alkylene glycol, for example ethylene glycol and/or propylene glycol and/or butylene glycol, and/or a polyol.

The weight ratio of the total amount of tungsten species (calculated on metal basis) provided to the first reactor, to the transition metal (calculated on metal basis) provided to the first reactor, may vary between wide ranges. The weight ratio of weight tungsten to the total weight of transition metal, all calculated on metal basis, as provided to the first reactor preferably ranges from equal to or more than 1:3000 to equal to or less than 50:1 (tungsten metal:transition metal weight ratio (wt/wt)). More preferably the weight ratio of weight tungsten to the total weight of transition metal, all calculated on metal basis, as provided to the first reactor preferably ranges from equal to or more than 1:200 to equal to or less than 50:1 (tungsten metal:transition metal weight ratio (wt/wt)).

The weight ratio of the total amount of tungsten species (calculated on metal basis) present in the first reactor, to the transition metal (calculated on metal basis) present in the first reactor, may also vary between wide ranges. The weight ratio of weight tungsten to the total weight of transition metal, all calculated on metal basis, as present in the first reactor preferably ranges from equal to or more than 1:3000 to equal to or less than 50:1 (tungsten metal:transition metal weight ratio (wt/wt)). More preferably the weight ratio of weight tungsten to the total weight of transition metal, all calculated on metal basis, as present in the first reactor preferably ranges from equal to or more than 1:200 to equal to or less than 50:1 (tungsten metal:transition metal weight ratio (wt/wt)).

More preferably the molar ratio of moles tungsten to the total moles transition metal, all calculated as metals, as present in the first reactor, preferably ranges from equal to or more than 1:1 to equal to or less than 25:1, more preferably from equal to or more than 2:1 to equal to or less than 20:1 (tungsten metal:transition metal (moles/moles)).

The concentration of tungsten compound, calculated as tungsten metal, based on the weight of carbohydrate source introduced into the first reactor, preferably ranges from equal to or more than 0.1 wt. %, more preferably from equal to or more than 1 wt. % to equal to or less than 35 wt. %, more preferably from equal to or more than 0.2 wt. %, even more preferably from equal to or more than 2 wt. % to equal to or less than 25 wt. %.

The concentration of transition metal introduced per hour into the first reactor, based on the weight of carbohydrate source introduced per hour into the first reactor, preferably ranges from equal to or more than 0.001 wt. %, more preferably from equal to or more than 0.01 wt. %, even more preferably from equal to or more than 0.1 wt. %, still more preferably from equal to or more than 0.2 wt. % to equal to or less than 2.0 wt. %, more preferably to equal to or less than 1.0 wt. %.

The first reactor can be any type of reactor known to be suitable for the production of ethylene glycol from a carbohydrate source. Preferably the first reactor is an agitated or mixing reactor. The first reactor can for example be a slurry reactor, an ebulated bed reactor, a fluidized bed reactor, a bubble reactor, an external recycle loop reactor or a continuous stirred tank reactor (CSTR) or another type of mechanically agitated reactor. Most preferably the first reactor is a continuously stirred tank reactor (CSTR). The use of a CSTR is very advantageous for the present process as the CSTR provides an excellent means for diluting the eventual concentration of the carbohydrate in the CSTR, whereas the feed stream may comprise a high concentration of carbohydrate. At the same time the alkylene glycols that are produced by the reaction of the carbohydrate provide a medium wherein tungsten compounds may be dissolved, thereby benefitting the catalytic activity of the tungsten catalyst component.

Step (ii) comprises reacting, in the first reactor, at a temperature in the range from equal to or more than 170° C. to equal to or less than 270° C., at least a portion of the carbohydrate source in the presence of the hydrogen, the solvent, the first heterogeneous catalyst and the homogeneous catalyst. Such reaction suitably yields at least ethylene glycol and sorbitol and optionally one or more other diols and/or other polyols. The residence time in the first reactor may vary. Preferably the mean residence time of the carbohydrate source in the first reactor is at least 1 min. (By mean residence time is herein understood the average time spent by a material flowing at a volumetric rate "u" through a volume "V", as further explained in the handbook "Modeling of Chemical Kinetics and Reactor Design" by A. Kayode Coker, published in 2001 by Butterworth Heinemann). Preferably the mean residence time of the carbohydrate source in the first reactor is in the range from equal to or more than 1 minutes to equal to or less than 6 hours, more preferably from equal to or more than 3 minutes to 2 hours, most preferable in the range from equal to or more than 5 minutes to equal to or less than 45 minutes. If the carbohydrate source reacts quickly, however, the mean residence time may also be shorter than 5 minutes and even shorter than 3 minutes. If a feed stream to the first reactor is used containing in the range of equal to or more than 20.0 wt. % of carbohydrate source, based on the total weight of the carbohydrate source and solvent, the mean residence time of the carbohydrate source in the first reactor is preferably equal to or more than 5 minutes, more preferably equal to or more than 10 minutes, and preferably equal to or less than 2 hours, more preferably equal to or less than 45 minutes. It is believed that such a longer mean residence time can advantageously assist to convert a feedstream with a higher concentration of carbohydrate source.

Preferably a continuous process is operated at a weight hourly space velocity (WHSV), expressed as the mass of carbohydrate source per mass of transition metal, expressed as metal, per hour, in the range of 0.01 to 100 hr$^{-1}$, preferably from 0.05 to 10 hr$^{-1}$. For practical purposes a WHSVB in the range between 0.5 to 2.0 hr$^{-1}$ can be used.

The hydrogen partial pressure applied during step (ii) preferably lies in the range from equal to or more than 1.0 Megapascal (MPa), preferably equal to or more than 2.0 MPA, more preferably equal to or more than 3.0 MPA to equal to or less than 16.0 MPA, preferably equal to or less than 12.0 MPA, more preferably equal to or less than 8.0 MPA. All pressures herein are absolute pressures.

The total pressure applied during step (ii) is suitably at least 1.0 MPA, preferably at least 2.0 MPA, more preferably at least 3.0 MPA The total pressure applied during step (ii) is suitably at most 16.0 MPA, more preferably at most 10.0 MPA Preferably the reactor is pressurized with hydrogen before addition of any starting material. The person skilled in the art will understand that the pressure at 20° C. will be lower than the actual pressure at the reaction temperature. The pressure applied during step (ii), when converted back to 20° C., preferably equals a pressure in the range from equal to or more than 0.7 MPA to equal to or less than 8.0 MPA As explained before, the pressure may be applied by hydrogen gas or a hydrogen-containing gas, optionally in combination with the partial pressures of the contents of the reaction mixture. When the reaction mixture is heated the total pressure during the reaction is suitably in the range from 1.0 MPA to 16.0 MPA It is preferred to maintain the partial hydrogen pressure at the reaction temperature during step (ii) within such range from 1.0 MPA to 16.0 MPa abs, preferably during the entire reaction. Therefore hydrogen or a hydrogen-containing gas is preferably introduced into the reaction mixture during reaction as explained above.

As indicated above, the pressure may be applied by hydrogen gas or a hydrogen-containing gas. When a hydrogen-containing gas is used, the hydrogen content in the hydrogen-containing gas is suitably up to 100 vol %. Most preferably a pure hydrogen gas is used to apply the pressure. During the reaction hydrogen is consumed. If the process is a continuous or semi-continuous process, the hydrogen is therefore preferably supplied in a continuous or semi-continuous manner.

The reaction can be carried out at a wide range of temperatures. In the first reactor at least a portion of the carbohydrate source is reacted with the hydrogen at a temperature in the range from equal to or more than 170° C. to equal to or less than 270° C. More preferably at least a portion of the carbohydrate source and hydrogen are reacted at a temperature in the range from equal to or more than 200° C. to equal to or less than 240° C. The first reactor may be brought to a temperature within these ranges before addition of any starting material and can be maintained at a temperature within the range.

The reaction in step (ii) is suitably yielding a first reactor product stream. This first reactor product stream suitably contains ethylene glycol, sorbitol and optionally one or more other by-products, such as erythritol. The first reactor product stream can suitably contain for example ethylene glycol (ethane-1,2-diol) and one or more by-products such as diethylene glycol (2,2'-oxydi(ethan-1-op) propylene glycol (propane-1,2-diol), glycerol (propane-1,2,3-triol), butane-1,2-diol, butane-1,3-diol, butane-2,3-diol, butane-1,4-diol, methanol, ethanol, propanol, butanol, sorbitol (hexane-1,2,3,4,5,6-hexol) and/or erythritol (butane-1,2,3,4-tetraol). Glycerol (propane-1,2,3-triol), sorbitol (hexane-1,2,3,4,5,6-hexol) and erythritol (butane-1,2,3,4-tetraol) are polyols having a high boiling point (i.e. a boiling point above 250° C. at atmospheric pressure of 0.1 Megapascal). As explained above, such polyols, having a boiling point above 250° C. at atmospheric pressure of 0.1 Megapascal, are herein also referred to as "heavy polyols".

Step (iii) comprises removing, from the first reactor, a first reactor product stream and separating from such first reactor product stream at least:
one ethylene glycol-rich fraction; and
one sorbitol-rich fraction containing concentrated homogeneous catalyst.

By a sorbitol-rich fraction is herein understood a fraction of the first reactor product stream comprising a higher concentration, e.g. a higher weight percentage, of sorbitol than the first reactor product stream itself. Such a sorbitol-rich fraction may herein also be referred to as sorbitol-enriched fraction. Preferably the sorbitol-rich fraction may include in the range from equal to or more than 5 wt. %, more preferably equal to or more than 10 wt. %, still more preferably equal to or more than 20 wt. % and most preferably equal to or more than 30 wt. % to equal to or less than 100 wt. % of sorbitol, suitably equal to or less than 90 wt. %, based on the total weight of the sorbitol-rich fraction.

By a ethylene glycol-rich fraction is herein understood a fraction of the first reactor product stream comprising a higher concentration, e.g. a higher weight percentage, of ethylene glycol than the first reactor product stream itself. Such a ethylene glycol-rich fraction may herein also be referred to as ethylene glycol-enriched fraction. Preferably the ethylene glycol-rich fraction may include in the range from equal to or more than 5 wt. %, more preferably equal to or more than 10 wt. %, still more preferably equal to or more than 20 wt. % and most preferably equal to or more than 30 wt. % to equal to or less than 100 wt. %, suitably equal to or less than 90 wt. % of ethylene glycol, based on the total weight of the ethylene glycol-rich fraction.

The separation can be carried out in any manner known to be suitable by one skilled in the art, including for example by evaporation and/or distillation.

More preferably step (iii) comprises separating, for example by distillation, at least a portion of the first reactor product stream into one or more, sorbitol-lean, fractions and at least one sorbitol-rich fraction. By a sorbitol-lean fraction is herein understood a fraction of the first reactor product stream comprising a lower concentration, e.g. a lower weight percentage, of sorbitol than the first reactor product stream itself. Such a sorbitol-lean fraction may herein also be referred to as sorbitol-depleted fraction. One or more of the sorbitol-lean fractions can suitably be enriched in alkylene glycol, for example ethylene glycol or propylene glycol. Suitably step (iii) can therefore comprise separating, for example by distillation, at least a portion of the first reactor product stream into at least:

one, ethylene glycol-rich, sorbitol-lean, fraction;
one or more other sorbitol-lean fractions; and
one sorbitol-rich fraction containing concentrated homogeneous catalyst.

The ethylene glycol-rich fraction may suitably be further purified to obtain a purified ethylene glycol product.

Before separating, for example in a distillation step, the sorbitol-rich fraction and/or the ethylene glycol-rich fraction, the first reactor product stream is preferably first degassed to remove any residual hydrogen. Subsequently the degassed first reactor product stream can be forwarded to one or more evaporators to separate one or more fractions containing or consisting of one or more C1-C4 mono-alkanols and/or water. By C1-C4 mono-alkanols are herein understood mono-alkanols comprising in the range from 1 to 4 carbon atoms. Examples of such one or more C1-C4 mono-alkanols include methanol, ethanol, propanol and/or butanol.

Preferably at least a portion of the remainder of the first reactor product stream (from which optionally hydrogen gas, C1-C4 mono-alkanols and/or water were already removed) is subsequently distilled into at least:

one or more sorbitol-lean, optionally alkylene glycol-rich, fractions; and
one sorbitol-rich fraction, containing concentrated homogeneous catalyst, sorbitol and optionally one or more other heavy polyols, such as glycerol and/or erythritol.

It is possible to distill merely a portion or to distill the whole of the first reactor product stream. The alkylene glycol is preferably ethylene glycol, propylene glycol, butanediol or a mixture of two or more of these.

The sorbitol-rich fraction can suitably be obtained by separating a fraction comprising compounds boiling at a temperature equal to or higher than 250° C. at a pressure of 0.1 Megapascal. Hence, suitably step (iii) comprises removing, from the first reactor, a first reactor product stream and separating from such first reactor product stream at least one fraction containing compounds boiling at a temperature equal to or higher than 250° C. at a pressure of 0.1 Megapascal and further containing concentrated homogeneous catalyst. Such a fraction, containing compounds boiling at a temperature equal to or higher than 250° C. at a pressure of 0.1 Megapascal, can herein also be referred to as "heavy fraction".

Suitably step (iii) can comprise separating, for example by distillation, at least a portion of the first reactor product stream into a fraction comprising compounds having a boiling point below 250° C. at a pressure of 0.1 Megapascal (also referred to as a "light fraction"); and a fraction comprising compounds having a boiling point equal to or higher than 250° C. at a pressure of 0.1 Megapascal (also referred to as a "heavy fraction"). Such light fraction can suitably be an ethylene glycol-rich fraction, whereas the such heavy fraction can suitably be a sorbitol-rich fraction. The person skilled in the art will understand that to separate the above mentioned compounds any distillation may actually be carried out at reduced pressure or even vacuum pressure, to allow one to make the separation at a temperature below 250° C.

This sorbitol-rich fraction or heavy fraction, preferably contains not only sorbitol, but also other heavy polyols, such as glycerol and erythritol. Preferably the fraction contains in the range from equal to or more than 0.5 wt. % to equal to or less than 99.5 wt. %, more preferably from equal to or more than 1.0 wt. % to equal to or less than 60.0 wt. % of heavy polyols (i.e. polyols boiling at a temperature equal to or higher than 250° C. at a pressure of 0.1 Megapascal), based on the total weight of such fraction. More preferably the fraction contains in the range from equal to or more than 0.5 wt. % to equal to or less than 99.5 wt. %, more preferably from equal to or more than 1.0 wt. % to equal to or less than 60.0 wt. % of sorbitol, based on the total weight of such fraction. Most preferably the sorbitol-rich fraction contains in the range from equal to or more than 2.0 wt. % to equal to or less than 50 wt. % of sorbitol, based on the total weight of the sorbitol-rich fraction.

The sorbitol-rich fraction further contains concentrated homogeneous catalyst. By concentrated homogeneous catalyst is herein understood homogeneous catalyst in a concentration higher than the concentration of homogeneous catalyst in the first reactor product stream. Preferably the concentration of homogeneous catalyst in the sorbitol-rich fraction ranges from equal to or more than 0.5 wt. % to equal to or less than 10.0 wt. %, more preferably 0.5 wt. % to equal to or less than 5.0 wt. %, and most preferably in the range from 1.0 wt. % to equal to or less than 5.0 wt. %, all calculated as tungsten metal, based on the total weight of the sorbitol-rich fraction. The homogeneous catalyst can be concentrated in the sorbitol-rich fraction in any manner known to be suitable by a person skilled in the art, including by evaporation and/or distillation of other compounds in the first reactor product stream.

The sorbitol and/or dissolved homogeneous catalyst cannot be easily distilled off. Hence the dissolved homogeneous catalyst can suitably be concentrated with the sorbitol in the sorbitol-rich fraction by evaporating and/or distilling off other compounds in the first reactor product steam. Preferably such sorbitol-rich fraction subsequently contains concentrated homogeneous catalyst, sorbitol and one or more other heavy polyols such as glycerol and/or erythritol. In addition, the sorbitol-rich fraction can contain other compounds.

Step (iv) comprises providing, to a second reactor, hydrogen and at least part of the sorbitol-rich fraction, containing concentrated homogeneous catalyst.

The second reactor can be any type of reactor known to be suitable for the production of ethylene glycol from a carbohydrate source. The second reactor can for example be a fixed bed reactor, a trickle flow reactor, a slurry reactor, an ebulated bed reactor, a fluidized bed reactor, a plug flow reactor, a bubble reactor, an external recycle loop reactor or a continuously stirred tank reactor (CSTR) or another type of mechanically agitated reactor. Most preferably the second reactor is a plug flow reactor. The first reactor and the second reactor can be the same or a different type of reactor. Preferably the process according to the invention is carried out in a combination of reactors where the first reactor is a continuously stirred tank reactor, whilst the second reactor is a plug flow reactor.

When introducing the sorbitol-rich fraction into the second reactor, the sorbitol-rich fraction becomes part of the reaction mixture in the second reactor and can subsequently be converted as described below.

Only part or the whole of the sorbitol-rich fraction can be provided to the second reactor.

In addition a fresh stream of hydrogen is provided to the second reactor. Suitably preferences for providing such hydrogen are the same as described previously for the first reactor. For example, the hydrogen can be supplied as a mixture of hydrogen and an inert gas in amounts as described previously for the first reactor.

When the second reactor is not a fixed bed reactor but a slurry reactor, the second heterogeneous catalyst can be provided separately to such second reactor as a slurry. Preferences for such a slurry are as mentioned above for a slurry of the first heterogeneous catalyst.

Optionally step (iv) may further comprise providing, to the second reactor, an additional solvent. Preferences for such additional solvent are as described above for the solvent.

Step (v) comprises reacting, in the second reactor, at a temperature in the range from equal to or more than 200° C. to equal to or less than 300° C., at least a part of the sorbitol-rich fraction, containing concentrated homogeneous catalyst, with the hydrogen in the presence of a second heterogeneous catalyst, which second heterogeneous catalyst contains one or more transition metals from groups 8, 9 and 10 of the Periodic Table of the Elements.

The residence time in the second reactor may vary. Preferably the mean residence time of the sorbitol-rich fraction in the second reactor is longer than the mean residence time of the carbohydrate source in the first reactor. Preferably, the mean residence time of the sorbitol-rich fraction in the second reactor is at least 1 hour. Preferably the mean residence time of the carbohydrate source is in the range of 1 hour to 6 hours, more preferably from 1 hour to 3 hours, most preferably 45 minutes to 90 minutes. It is believed that the conversion of heavy polyol by-products such as sorbitol and/or erythritol benefits from a longer mean residence time. Preferably the second reactor is a plug flow reactor operated at a weight hourly space velocity (WHSV), expressed as the mass of carbohydrate source per mass of transition metal, expressed as metal, per hour, in the range of 0.01 to 100 hr$^{-1}$, preferably from 0.05 to 10 hr$^{-1}$.

The preferences for the hydrogen partial pressure applied in the second reactor during step (v) are the same as for the hydrogen partial pressure applied in the first reactor during step (ii). Also preferences for the total pressure applied in the second reactor are the same as for the first reactor.

The reaction in step (v) is preferably carried out at a temperature in the range from equal to or more than 220° C. to equal to or less than 260° C.

More preferably the temperature T2 applied during the reaction in the second reactor in step (v) is equal to or more than the temperature T1 applied during the reaction in the first reactor in step (ii).

The second heterogeneous catalyst contains one or more transition metals from groups 8, 9 and 10 of the Periodic Table of the Elements. The second heterogenous catalyst can be the same as or different from the first heterogeneous catalyst. Preferably, however, the composition of the second heterogeneous catalyst is similar to that of the first heterogeneous catalyst and preferences for the transition metal and carrier are as for the first heterogeneous catalyst as described above. Preferably, the second heterogeneous catalyst contains ruthenium and/or nickel as the transition metal and activated carbon as the carrier. That is most preferably the heterogeneous catalyst comprises ruthenium and/or nickel, supported on activated carbon. Most preferably the second reactor is a plug flow reactor wherein the second heterogeneous catalyst is present as a fixed bed.

The homogenous catalyst in step (v) is the same as the homogeneous catalyst in step (ii). Advantageously, however, the homogeneous catalyst in step (v) can be present in a higher concentration than in step (ii). That is, the concentration of homogeneous catalyst in the reaction mixture in the second reactor of step (v) can suitably be higher than the concentration of homogeneous catalyst in the reaction mixture in the first reactor of step (ii).

Preferences for the concentration of homogeneous catalyst are as described above for the sorbitol-rich fraction. Most preferably the concentration of homogeneous catalyst in the reaction mixture in the second reactor ranges from equal to or more than 0.5 wt. % to equal to or less than 5.0 wt. %, calculated as tungsten metal, based on the total weight of the reaction mixture.

The weight ratio between the total amount of tungsten compound (calculated on metal basis) present in the second reactor and the transition metal (calculated on metal basis) present in the second reactor may vary between wide ranges. When the second reactor is a CSTR or slurry reactor, the weight ratio between the total amount of tungsten compound (calculated on metal basis) present in the second reactor and the transition metal (calculated on metal basis) present in the second reactor is preferably higher than the weight ratio between the total amount of tungsten compound (calculated on metal basis) present in the first reactor and the transition metal (calculated on metal basis) present in the first reactor. Also, when the second reactor is a CSTR or slurry reactor, the molar ratio of moles tungsten to the total moles transition metal, all calculated as metals, is preferably higher in the second reactor than in the first reactor.

If desired additional solvent can be added to the reaction mixture in the second reactor in step (v). Preferences for such additional solvent are as mentioned above for the first reactor of step (ii). Most preferably any additional solvent is water.

Advantageously the second reactor can be operated at less than full conversion of the sorbitol, preferably at a sorbitol conversion in the range from equal to or more than 50 wt. % to equal to or less than 90 wt. %. This advantageously allows part of the sorbitol to remain as solvent for the homogeneous catalyst when optionally recycling at least a portion of the second reactor product stream to the first reactor.

Step (vi) comprises removing a second reactor product stream from the second reactor and optionally recycling at least a portion of the second reactor product stream to the first reactor. As indicated above, the second reactor product stream can advantageously be used as a stream for the addition of dissolved homogeneous catalyst to the first reactor.

Hence, preferably the process according to the invention further comprises recycling at least a portion of the homogeneous catalyst from the second reactor back to the first reactor.

Suitably the second reactor product stream can be degassed to removed hydrogen before recycling. In addition, it may be desirable to remove at least part of the water and C1-C4 mono-alkanols (e.g. methanol, ethanol, propanol and/or butanol), before recycling.

Figure 1:
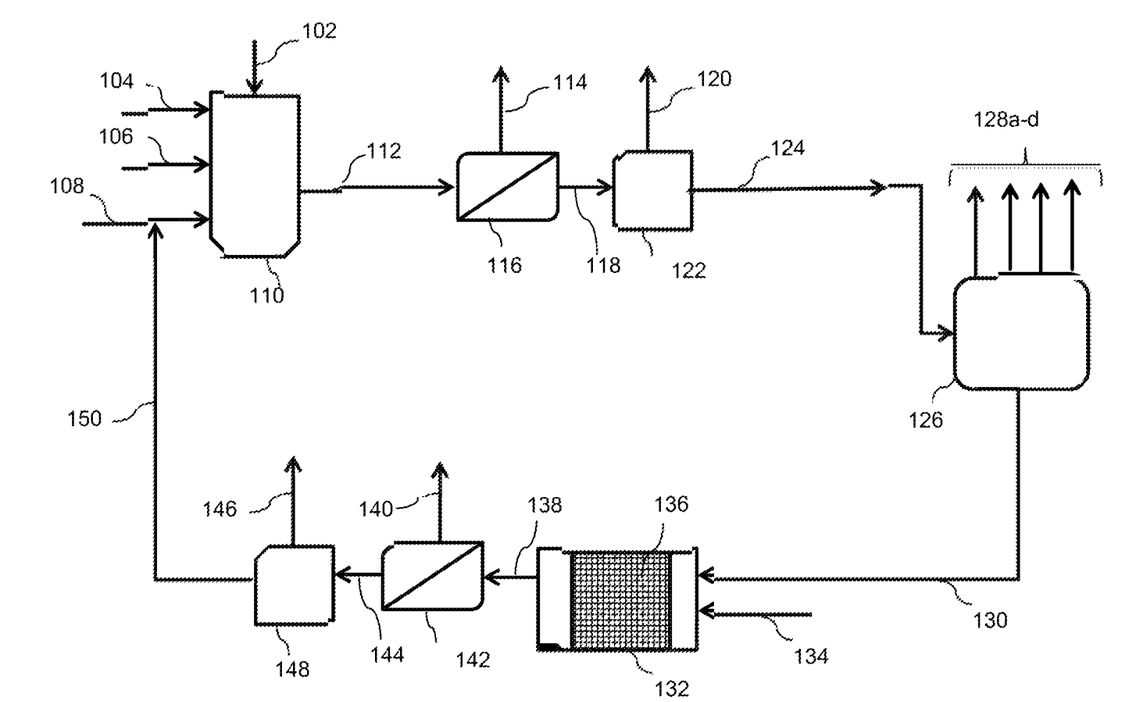
FIG. 1 shows an example of the process according to the invention.

A non-limiting example of the process of the invention is shown in FIG. 1.

In FIG. 1, a stream of hydrogen (102), a stream comprising a homogeneous catalyst solution (108), a stream comprising a slurry of a first heterogeneous catalyst (106) and a feed stream comprising a carbohydrate source (104) are provided to a continuously stirred tank reactor (110). In this example, the continuously stirred tank reactor (CSTR) is acting as a first reactor; the homogeneous catalyst solution (108) suitably comprises tungstic acid, sodium hydroxide and/or sodium tungstate in glycerol and water; and the first heterogeneous catalyst (106) suitably comprises 5 wt. % Ruthenium on active carbon slurried in water. The carbohydrate source (104) suitably comprises a solution of glucose in water, alkylene glycols and other diols and polyols). In addition homogeneous catalyst is recycled from the second reactor via stream (150). This stream (150) suitably comprises homogeneous catalyst dissolved in amongst others alkylene glycols, other diols and/or other polyols.

In the CSTR (110) the glucose is reacted with the hydrogen at a temperature of about 220° C. in the presence of the homogeneous catalyst and the heterogeneous catalyst. The CSTR (110) is maintained at a total pressure of about 6.5 Megapascal. The water, alkylene glycols and other diols and/or other polyols are acting as solvent. The reaction mixture contains an average concentration of tungsten metal corresponding to about 0.4 wt. % tungstic acid, based on the total weight of the reaction mixture. A first reactor product stream (112) is removed from the CSTR (110). This exemplary first reactor product stream (112) suitably contains amongst others hydrogen, ethylene glycol, propylene glycol, erythritol, sorbitol, water, methanol, ethanol, propanol and butanol. Further, this first reactor product stream (112) comprises an amount of tungsten metal corresponding to about 0.4 wt. % tungstic acid, based on the total weight of the first reactor product stream (112). In addition the first reactor product stream may or may not contain particles of first heterogeneous catalyst. If such particles of first heterogeneous catalyst are present, these particles may separated from the first reactor product stream by filtration and recycled to the CSTR (110). Subsequently a stream of hydrogen (114) is removed from the first reactor product stream (114) in degasser unit (116). From the resulting stream (118), a stream of C1-C4 mono-alkanols (such as methanol, ethanol, propanol and butanol) (120) and part of the water are removed in evaporator unit (122). The resulting stream (124) is subsequently forwarded to a distillation unit (126), where stream (124) is separated into four sorbitol-lean fractions (128a, 128b, 128c and 128d, all containing compounds having a boiling point at 0.1 Megapascal below 250° C.) and a sorbitol-rich fraction (130) containing compounds having a boiling point at 0.1 Megapascal above 250° C. Tungsten species such as tungstic acid, tungsten bronze, sodium tungstate or derivatives thereof remain dissolved in the sorbitol-rich fraction (130). As a result of distilling off other components, the concentration of tungsten metal increases and such sorbitol-rich fraction (130) suitably contains an amount of tungsten metal corresponding to about 1.9 wt. % tungstic acid, based on the total weight of the sorbitol-rich fraction (130).

The sorbitol-rich fraction (130) is forwarded to a plug flow reactor (132), where it is contacted with a fresh stream of hydrogen (134). In this example, the plug flow reactor (PFR) is acting as a second reactor. The PFR contains a fixed bed (136) of a second heterogeneous catalyst consisting of 5 wt. % Ruthenium on activated carbon (5 wt. % Ru/AC). In the PFR (132), the sorbitol is reacted with the hydrogen at a temperature of about 240° C. in the presence of the homogeneous catalyst and the second heterogeneous catalyst to yield a second reactor product stream (138). This second reactor product stream (138) is removed from the PFR (132). The sorbitol itself and other components of the sorbitol-rich fraction are acting as a solvent. The second reactor product stream suitably comprises hydrogen, propane, methanol, tetrahydrofuran, ethanol, propanol, butanol and water in addition to ethylene glycol and propylene glycol. Preferably the PFR is not operated at full conversion, but at a conversion of about 70 wt. % of the total amount of sorbitol, allowing about 30 wt. % of the sorbitol to remain unconverted. Suitably the second product stream (138) is forwarded to a degasser unit (142) to remove a stream of hydrogen (140). From the resulting stream (144), a stream of C1-C4 mono-alkanols (such as methanol, ethanol, propanol and butanol) (146) and part of the water are removed in evaporator unit (148). The resulting stream (150) can advantageously be recycled to the first reactor (110).

The process according to the invention is further illustrated by the following non-limiting example.

Example 1

The process as illustrated in FIG. 1 has been demonstrated using computational modeling software ASPEN PLUS version 8.8 (ASPEN is a trademark) in conjunction with databanks APV88 PURE32, APV88 AQUEOUS, APV88 SOLIDS, APV88 INORGANIC, NISTV88 NIST-TRC as available within ASPEN PLUS 8.8. and in further conjunction with VLE data for ethylene glycol, propylene glycol and butylene glycol mixtures obtainable from the Dortmund Data Bank. The concentration of tungsten compounds was presumed to be a concentration, corresponding to 0.4 wt. % tungstic acid in the CSTR reactor, acting as first reactor and a concentration of tungsten compounds, corresponding to 1.9 wt. % tungstic acid in the Plug Flow Reactor, acting as second reactor. The simulated heterogeneous catalyst was presumed to be 5 wt. % Ruthenium on active carbon slurried in water.

The composition of the stream of hydrogen (102), and a feed stream comprising a carbohydrate source (104), as supplied to the simulated CSTR reactor, are listed in table 1A. In addition the composition of a recycle stream (150) also supplied to the simulated CSTR reactor is listed. The compositions of the resulting first product stream (112), the product stream after H2, partial H2O and C1-C4 mono-alkanol removal (125), a 1st sorbitol-lean fraction (128a), a 2nd sorbitol-lean fraction (128*b*), a 3$^{rd}$ sorbitol-lean fraction (128*c*), a 4th sorbitol-lean fraction (128*d*), a sorbitol-rich fraction (130) and a Second reactor product stream (138) are all listed in table 1B.

From the second reactor product stream (138) suitably hydrogen and light boiling components such as the C1-C4 alkanols and part of the water are removed, leaving a recycle stream (150) which is recycled to the first reactor. The composition of recycle stream (150) was already provided in table 1A. All listed amounts in tables 1A and 1B are in kilograms per hour (kg/hour). In the tables the following abbreviations are used:

| | | |
|---|---|---|
| H2 | : | Hydrogen |
| PROP | : | C1-C6 Alkanes (in the Aspen model used, propane was used as a "standard compound" for all alkanes comprising in the range from 1 to 6 carbon atoms) |
| MEOH | : | Methanol |
| THF | : | Tetrahydrofuran |
| ETOH | : | Ethanol |
| PROH-1 | : | 1-Propanol |
| PROH-2 | : | 2-Propanol (isopropyl-alcohol) |
| BUOH | : | n-Butanol |
| H2O | : | water |
| GLYALD | : | Glycol-aldehyde (hydroxyacetaldehyde) |
| HOACET | : | Hydroxy acetone (1-hydroxypropan-2-one) |
| THF-ALC | : | Tetrahydrofurfuryl - alcohol |
| PG | : | 1,2-Propanediol (propylene glycol) |
| BG | : | 1,2-Butanediol |
| EG | : | 1,2 -Ethanediol (ethylene glycol) |
| 1,3-BG | : | 1,3-Butanediol |
| GL | : | Glycerol (Propane-1,2,3-triol) |
| ET | : | Meso-Erythritol (butane-1,2,3,4-tetraol) |
| SB | : | sorbitol (hexane-1,2,3,4,5,6-hexol) |
| GLU | : | DEXTROSE (D-Glucose) |
| DIETHYL | : | Diethylene glycol (2,2'-oxydi(ethan-1-ol)) |
| PG-13 | : | 1,3-Propanediol |
| BG-14 | : | 1,4-Butanediol |

TABLE 1A

Composition of the feed streams (all in kg/hour)

| Component | Glucose feed stream (104) | Hydrogen stream (102) | Recycle stream (150) |
|---|---|---|---|
| H2 | 0 | 3212 | 0 |
| PROP | 0 | 0 | 0 |
| MEOH | 0 | 0 | 0 |
| THF | 0 | 0 | 0 |
| ETOH | 0 | 0 | 0 |
| PROH-1 | 0 | 0 | 0 |
| PROH-2 | 0 | 0 | 0 |
| BUOH | 0 | 0 | 14 |
| H2O | 39470 | 0 | 2681 |
| GLYALD | 0 | 0 | 93 |
| HOACET | 0 | 0 | 0 |
| THF-ALC | 0 | 0 | 0 |
| PG | 0 | 0 | 13 |
| BG | 0 | 0 | 0 |
| EG | 0 | 0 | 402 |
| 1,3-BG | 0 | 0 | 2 |
| GL | 0 | 0 | 358 |
| ET | 0 | 0 | 10567 |
| SB | 0 | 0 | 15022 |
| GLU | 92097 | 0 | 1 |
| DIETHYL | 0 | 0 | 64242 |
| PG-13 | 0 | 0 | 292 |
| BG-14 | 0 | 0 | 177 |

TABLE 1B

Composition of the product and fraction streams (all in kg/hour)

| Component | First reactor product stream (112) | Product stream after H2, partial H2O and C1-C4 mono-alkanol removal (125) | 1$^{st}$ Sorbitol-lean fraction (128a) | 2$^{nd}$ Sorbitol-lean fraction (128b) | 3$^{rd}$ Sorbitol-lean fraction (128c) | 4$^{th}$ Sorbitol-lean fraction (128d) | Sorbitol-rich fraction (130) | Second reactor product stream (kg/hour) (138) |
|---|---|---|---|---|---|---|---|---|
| H2 | 125 | 0 | 0 | 0 | 0 | 0 | 0 | 468 |
| PROP | 0 | 0 | 0 | 0 | 0 | 0 | 0 | 1878 |
| MEOH | 1763 | 0 | 0 | 0 | 0 | 0 | 0 | 88 |
| THF | 0 | 0 | 0 | 0 | 0 | 0 | 0 | 222 |
| ETOH | 1197 | 0 | 0 | 0 | 0 | 0 | 0 | 44 |
| PROH-1 | 1042 | 0 | 0 | 0 | 0 | 0 | 0 | 92 |
| PROH-2 | 104 | 0 | 0 | 0 | 0 | 0 | 0 | 23 |
| BUOH | 28 | 0 | 0 | 0 | 0 | 0 | 0 | 237 |
| H2O | 279875 | 59 | 59 | 0 | 0 | 0 | 0 | 3647 |
| GLYALD | 4349 | 3792 | 3790 | 2 | 0 | 0 | 0 | 95 |
| HOACET | 176 | 112 | 112 | 0 | 0 | 0 | 0 | 0 |
| THF-ALC | 0 | 0 | 0 | 0 | 0 | 0 | 0 | 0 |
| PG | 11038 | 11012 | 22 | 10963 | 28 | 0 | 0 | 13 |
| BG | 1290 | 1289 | 0 | 0 | 1225 | 64 | 0 | 0 |
| EG | 64228 | 64210 | 0 | 13 | 1244 | 62700 | 254 | 408 |
| 1,3-BG | 33 | 33 | 0 | 0 | 0 | 27 | 7 | 2 |
| GL | 358 | 358 | 0 | 0 | 0 | 0 | 358 | 364 |
| ET | 15466 | 15466 | 0 | 0 | 0 | 0 | 15466 | 10728 |
| SB | 21893 | 21893 | 0 | 0 | 0 | 0 | 21893 | 15251 |
| GLU | 92 | 92 | 0 | 0 | 0 | 0 | 92 | 1 |
| DIETHYL | 59753 | 59753 | 0 | 0 | 0 | 0 | 59753 | 65221 |
| PG-13 | 318 | 318 | 0 | 0 | 0 | 27 | 291 | 297 |
| BG-14 | 208 | 206 | 0 | 0 | 0 | 0 | 206 | 180 |

Example 2

A continuously stirred tank reactor (CSTR) provided with a mechanical stirrer and having a volume of about 6 ml was filled with 500 milligrams (mg) of a wetted heterogeneous catalyst (50 wt % moisture). The wetted heterogeneous catalyst contained 250 mg (calculated on dry basis) of a heterogeneous catalyst comprising 5 wt % ruthenium on activated carbon, the remainder being water. Subsequently the CSTR was completely filled with water.

An aqueous feed solution was prepared, containing about 10 wt. % glucose, about 0.15 wt. % tungstic acid (H2WO4), about 19 wt. % Glycerol and about 0.18 g/l NaOH, by combining the components as illustrated in Table 2A.

A feed stream of the aqueous feed solution of Table 2A was provided at a flowrate of 0.25 ml/min to a continuously stirred tank reactor (CSTR) over a period of about 5 hours. The hydrogen flow applied was 100 normalized milliliters per minute (Nml/min).

The CSTR was stirred at a stirrer speed of 1500 rpm. The reaction temperature was kept at about 220° C. The hydrogen pressure was kept at about 80 bar (corresponding to about 8 Megapascal). The mean residence time of the liquid in the reactor was therefore about 24 min. On average, the ruthenium to tungsten weight ratio, calculated on the basis of the metals, was about 3.8, the tungsten (calculated as the metal) to glucose weight ratio was about 0.03, and the ruthenium (calculated as the metal) to glucose weight ratio was about 0.04 The CSTR was allowed to operate until steady state was reached. The effluent of such steady state reaction was analyzed and the results are summarized in Table 2B. The conversion of glucose was found to be constant at a conversion rate of more than 99 wt. % (conversion calculated based on the glucose being supplied to the reactor). The concentrations and weight percentages of ethylene glycol (EG), propylene glycol (PG), butylene glycol (BG) and sorbitol (SB) were determined by means of High Performance Liquid Chromatography (HPLC). The selectivities (in wt. %) were calculated in amounts of ethylene glycol, propylene glycol, butylene glycol and sorbitol, as the weight percentage in the reactor effluent divided by the weight percentage of glucose being introduced into the CSTR.

TABLE 2A

Composition of the aqueous feed solution

| Component | Weight in grams (g)/microliters (μl) | Weight percentage in the feed (wt. %) |
|---|---|---|
| Glucose | 20 g | 10 |
| Water | 141.7 g | 71 |
| 5 wt. % tungstic acid (H2WO4) dissolved in Glycerol | 6 g | 3 |
| Glycerol | 32.3 g | 16 |
| 50 wt. % Sodium hydroxide (NaOH) dissolved in water | 48 μl | <1 |

TABLE 2B

Conversion and composition of the reactor effluent

| | Selectivity (in wt. %) | Weight percentage in the effluent (wt. %) |
|---|---|---|
| Conversion | >99 | |
| Ethylene glycol | 44 | 4.4 wt. % |
| Propylene glycol | 16 | 1.6 wt. % |
| Butylene glycol | 1.6 | 0.2 wt. % |
| Sorbitol | 26 | 2.6 wt. % |

Subsequently the effluent of the CSTR, as listed in Table 2B, can be distilled in a distillation section comprising one or more distillation columns (not actually carried out) such as to prepare:
one ethylene glycol-rich fraction; and
one sorbitol-rich fraction containing concentrated homogeneous catalyst.

Example 3

To demonstrate the conversion of sorbitol in the second reactor, a feed that mimics the composition of a sorbitol-containing stream coming out of a distillation section, such as the one illustrated as (126) in FIG. 1, was prepared.

20.18 Grams erythritol, 35.23 grams sorbitol, 11.14 grams glucose, 50.25 grams ethylene glycol, and 196.33 grams of glycerol were mixed at 120° C. for 1 hour. Once the erythritol, sorbitol, glucose and glycerol were dissolved in the ethylene glycol, and while the mixture was still being heated, 202.43 grams of a tungstic acid containing glycerol solution was added to the mixture. The tungstic acid containing glycerol solution contained 5 wt. % tungstic acid ($H_2WO_4$) and 95 wt. % glycerol, based on the total weight of the glycerol solution. (The 5 wt. % $H_2WO_4$ in glycerol solution was prepared by mixing 12.63 grams $H_2WO_4$ with 237.80 grams of glycerol and keeping it under reflux at 180° C. for 3 hours). Subsequently also 2134 microliter of an aqueous 50 wt. % sodiumhydroxide (NaOH) solution was added to form a feed composition. An overview of the feed composition is provided in Table 3A.

TABLE 3A

Feed composition

| Component | Weight percentage in the feed (wt. %) |
|---|---|
| erythritol | 4 |
| sorbitol | 7 |
| glucose | 2 |
| ethylene glycol | 10 |
| glycerol | 75 |
| H2WO4 | 2 |

The above feed was provided to a small-scale plug flow reactor. This plug flow reactor comprised an essentially vertically arranged stainless steel tubular reactor with a diameter of 0.98 centimeters and 45 centimeters length, giving a total internal volume of 33.75 milliliters. The reactor was placed inside of an electric oven that kept it at the operating temperature. The reactor had an isothermal zone with a length of 17 centimeter, giving an effective reactor volume of 12 milliliters. A frit was inserted into the reactor in order to keep the catalyst bed in the isothermal zone. Approximately one centimeter of quart wool was placed on the frit surface. Then the isothermal zone of the reactor was filled up with 16 cm of the heterogeneous catalyst comprising 5 wt. % Ruthenium on carbon extrudates (approximately 5 grams). The remainder (top) of the reactor was filled up with an inert material.

Once the catalyst was loaded into the reactor, the reactor was placed in the oven and the catalyst was reduced prior to the reaction by keeping the catalyst under a flow of nitrogen for 1 hour, subsequently heating the catalyst up to 300° C. under a flow of hydrogen (heating at a temperature rate of 5° C./minute) and keeping the catalyst at 300° C. under such flow of hydrogen for a period of 4 hours. Hereafter the catalyst was kept under a flow of nitrogen until the reaction was started.

The feed was provided to the reactor at a Liquid hourly space velocity (LHSV) of 0.75 $h^{-1}$ and reacted in the isothermal zone of the reactor at a temperature of 220° C., a reactor pressure of 50 bar (corresponding to 5 Megapascal) and a hydrogen to polyol molar ratio of 5:1. Both the feed as well as the hydrogen were introduced via the top of the reactor.

The concentration of tungstic acid in the feed was about 2 wt. %, based on the total weight of the feed.

Once the operating parameters were stable, the experiment was started (t=0). Samples were taken from the effluent of the reactor at t=0 hours, t=2 hours, t=4 hours, t=21 hours, t=23 hours, t=25 hours and t=28 hours.

It was found that the process remained unstable during the first 4 hours and only became stable thereafter. The conversions and yields after 4 hours, i.e. at t=21 hours, t=23 hours, t=25 hours and t=28 hours are summarized in Table 3B.

The samples were analyzed by liquid chromatography (LC) and gas chromatography (GC) in order to determine the conversion of the components present in the feed and the formation of the potential products as summarized in Table 3B.

As illustrated by Table 3B, conversions of the main components in the feed were as follows:
Gycerol: about 34 wt. %
Glucose: about 100 wt. %
Sorbitol: about 50 wt. %
Erythritol: about 45 wt. %.

The conversions of ethylene glycol were negative, illustrating that there is actually ethylene glycol formed during the process.

As illustrated by the results summarized in Table 3B, the use of concentrated homogeneous catalyst results in a conversion of the so-called heavy polyols glycerol, sorbitol and erithrytol.

Example 4

To demonstrate the conversion of sorbitol in the second reactor, a feed that mimics the composition of a sorbitol-containing stream coming out of a distillation section, such as the one mentioned under example 2, was prepared.

127.02 Grams erythritol, 181.83 grams sorbitol, 0.90 grams glucose, 2.88 grams ethylene glycol, 184.76 grams of glycerol, 2.42 grams 1,3-propylene glycol and 1.94 grams 1,4-butylene glycol were mixed at 120° C. for two hour. Once the erythritol, sorbitol, glucose, ethylene glycol, 1,3-propylene glycol, 1,4-butylene glycol and glycerol were mixed into a homogeneous mixture, while the mixture was still being heated, 323.04 grams of a tungstic acid containing glycerol solution was added to the mixture. The tungstic acid containing glycerol solution contained 5 wt % tungstic acid ($H_2WO_4$) and 95 wt % glycerol, based on the total weight of the glycerol solution. (The 5 wt % $H_2WO_4$ in glycerol solution was prepared by mixing 35.25 grams $H_2WO_4$ with 666.47 grams of glycerol and keeping it under reflux at 180° C. for 3 hours). Subsequently also 3414.4 microliter of an aqueous 50 wt % sodiumhydroxide (NaOH) solution was added to form a feed composition. An overview of the feed composition is provided in Table 4A.

TABLE 4A

Feed composition

| Component | Weight percentage in the feed (wt. %) |
|---|---|
| Ethylene glycol | 0.35 |
| Glycerol | 59.61 |
| Erythritol | 15.40 |
| Sorbitol | 22.05 |
| Glucose | 0.11 |
| 1,3 Propylene glycol | 0.29 |
| 1,4 Butylene glycol | 0.24 |
| Tungstic Acid (H2WO4) | 1.96 |

The above feed was provided to a small-scale plug flow reactor. This plug flow reactor comprised an essentially vertically arranged stainless steel tubular reactor with a diameter of 0.98 centimeters and 45 centimeters length, giving a total internal volume of 33.75 milliliters. The reactor was placed inside of an electric oven that kept it at the operating temperature. The reactor had an isothermal zone with a length of 17 centimeter, giving an effective reactor volume of 12 milliliters. A frit was inserted into the

TABLE 3B

Results

| Sample taken at sampling time (in hours): | Glycerol conversion (wt. %) | Glucose conversion (wt. %) | Sorbitol conversion (wt. %) | Erythritol conversion (wt. %) | Ethylene glycol conversion (wt. %) ** | 1,2 propanediol (propylene glycol) yield (wt. %) | 1,3 propanediol yield (wt. %) | C1-C4 mono-alkanol yield * (wt. %) |
|---|---|---|---|---|---|---|---|---|
| 21 | 34.4 | 100.0 | 51.3 | 45.5 | −3.0 | 9.5 | 0.9 | 2.5 |
| 23 | 35.8 | 100.0 | 52.0 | 44.6 | 0.0 | 9.2 | 0.6 | 2.5 |
| 25 | 32.8 | 100.0 | 49.7 | 42.4 | −5.0 | 9.3 | 1.0 | 2.8 |
| 28 | 33.0 | 100.0 | 50.2 | 45.2 | −3.0 | 9.1 | 0.9 | 2.0 |

* Combined yield of methanol, ethanol, 2-propanol, 1-propanol and n-butanol.
** The conversions of ethylene glycol are negative, illustrating that there is actually ethylene glycol formed during the process.

reactor in order to keep the catalyst bed in the isothermal zone. Approximately one centimeter of quart wool was placed on the frit surface. Then the isothermal zone of the reactor was filled up with 8 cm of the heterogeneous catalyst comprising 10 wt % Ruthenium on carbon extrudates (approximately 3.5 grams). The remainder (top) of the reactor was filled up with an inert material.

Gycerol: about 62-75 wt %
Glucose: about 100 wt %
Sorbitol: about 75-87 wt %
Erythritol: about 68-81 wt %.

The conversions of ethylene glycol were negative, illustrating that there is actually ethylene glycol formed during the process.

TABLE 4B

Results (yields are referring to yield we mean % of the component in the product mixture)

| Sample taken at sampling time (in hours): | Glycerol conversion (wt. %) | Glucose conversion (wt. %) | Sorbitol conversion (wt. %) | Erythritol conversion (wt. %) | Ethylene glycol yield ** (wt. %) | 1,2 propanediol (propylene glycol) yield (wt. %) | 1,3 propanediol yield (wt. %) | C1-C4 mono- alkanol yield * (wt. %) |
|---|---|---|---|---|---|---|---|---|
| 43 | 75.7 | 100.0 | 87.2 | 81.9 | 7 | 12.3 | 0.7 | 4.8 |
| 45 | 74.9 | 100.0 | 86.4 | 81.1 | 6 | 12.2 | 0.7 | 4.7 |
| 47 | 73.2 | 100.0 | 85.0 | 79.5 | 6 | 12.0 | 0.6 | 4.4 |
| 49 | 72.3 | 100.0 | 84.3 | 78.5 | 6 | 12.3 | 0.0 | 4.5 |
| 51 | 71.3 | 100.0 | 83.4 | 77.4 | 6 | 11.5 | 0.6 | 4.4 |
| 68 | 67.6 | 100.0 | 80.3 | 73.5 | 6 | 10.6 | 0.6 | 4.3 |
| 70 | 67.4 | 100.0 | 80.3 | 73.5 | 6 | 10.8 | 0.6 | 4.1 |
| 72 | 65.9 | 100.0 | 79.1 | 72.7 | 6 | 10.7 | 0.6 | 3.6 |
| 75 | 65.8 | 100.0 | 78.7 | 71.8 | 6 | 10.2 | 0.8 | 3.7 |
| 91 | 63.8 | 100.0 | 76.4 | 69.5 | 5 | 9.7 | 0.7 | 3.4 |
| 93 | 63.9 | 100.0 | 76.6 | 69.6 | 6 | 9.9 | 0.7 | 3.7 |
| 95 | 63.4 | 100.0 | 76.1 | 69.3 | 6 | 9.9 | 0.7 | 3.2 |
| 97 | 63.9 | 100.0 | 76.6 | 69.6 | 5 | 9.8 | 0.7 | 3.9 |
| 98 | 62.7 | 100.0 | 75.6 | 68.4 | 5 | 9.6 | 0.7 | 3.6 |

\* Combined yield of methanol, ethanol, 2-propanol, 1-propanol and n-butanol.
\*\* The conversions of ethylene glycol are negative, illustrating that there is actually ethylene glycol formed during the process.

Once the catalyst was loaded into the reactor, the reactor was placed in the oven and the catalyst was reduced prior to the reaction by keeping the catalyst under a flow of nitrogen for one hour, subsequently heating the catalyst up to 300° C. under a flow of hydrogen (heating at a temperature rate of 5° C./minute) and keeping the catalyst at 300° C. under such flow of hydrogen for a period of 4 hours. Hereafter the catalyst was kept under a flow of nitrogen until the reaction was started.

The feed was provided to the reactor at a liquid hourly space velocity (LHSV) of 0.5 h$^{-1}$ and reacted in the isothermal zone of the reactor at a temperature of 240° C., a reactor pressure of 50 bar (corresponding to 5 Megapascal) and a hydrogen to polyol molar ratio of about 5.7:1 Both the feed as well as the hydrogen were introduced via the top of the reactor.

The concentration of tungstic acid in the feed was about 2 wt %, based on the total weight of the feed.

Once the operating parameters were stable, the experiment was started (t=0). Samples were taken from the effluent of the reactor at t=0 hours, t=2 hours, t=3 hours, t=20 hours, t=21 hours, t=23 hours t=26 hours, t=43 hours, t=45 hours, t=47 hours, t=49 hours, t=51 hours, t=68 hours, t=70 hours, t=72 hours, t=75 hours, t=91 hours, t=93 hours, t=95 hours, t=97 hours and t=98 hours.

It was found that on or before t=43 hours the process became stable. The conversions and yields as of such t=43 hours are listed in Table 4B below.

The samples were analyzed by liquid chromatography (LC) and gas chromatography (GC) in order to determine the conversion of the components present in the feed and the formation of the potential products as summarized in Table 4B.

As illustrated by Table 4B, conversions of the main components in the feed were as follows:

Example 5

A continuously stirred tank reactor (CSTR) provided with a mechanical stirrer and having a volume of about 6 ml was filled with 500 milligrams (mg) of a wetted heterogeneous catalyst (50 wt % moisture). The wetted heterogeneous catalyst contained 250 mg of a heterogeneous catalyst comprising 5 wt % ruthenium on activated carbon calculated on dry basis, the remainder being water. Subsequently the CSTR was completely filled with water.

An aqueous feed solution was prepared, containing glucose, glycerol, water, NaOH and the effluent stream from plug flow reactor of example 4 containing 1.62 wt % tungsten (calculated as metal W) by combining the components as illustrated in Table 5A.

A feed stream of the aqueous feed solution of Table 5A was provided at a flowrate of 0.25 ml/min to the continuously stirred tank reactor (CSTR) over a period of about 5 hours.

The hydrogen flow applied was 100 normalized milliliters per minute (Nml/min). The CSTR was stirred at a stirrer speed of 1500 rpm. The reaction temperature was kept at about 220° C. The hydrogen pressure was kept at about 80 bar (corresponding to about 8 Megapascal). The mean residence time of the liquid in the reactor was therefore about 24 min. On average, the ruthenium to tungsten weight ratio, calculated on the basis of the metals, was about 1.9, the tungsten (calculated as the metal) to glucose weight ratio was about 0.011, and the ruthenium (calculated as the metal) to glucose weight ratio was about 0.020 The CSTR was allowed to operate until steady state was reached. The effluent of such steady state reaction was analyzed. The conversion of glucose was found to be constant at a conversion rate of more than 99% (conversion calculated based on the glucose being supplied to the reactor). The concentrations and weight percentages of ethylene glycol (EG), propylene glycol (PG), butylene glycol (BG) and sorbitol (SB) were determined by means of High Performance Liquid Chromatography (HPLC). The selectivities (in wt. %) were calculated in amounts of ethylene glycol, propylene glycol, butylene glycol and sorbitol, as the weight percentage in the reactor effluent divided by the weight percentage of glucose being introduced into the CSTR.

TABLE 5A

Composition of the aqueous feed solution

| Component | Weight in grams (g) |
| --- | --- |
| Glucose | 20 |
| Water | 138.8 |
| Effluent stream from example 4 containing 1.62 wt % W in a polyol mixture | 13.75 |
| Glycerol | 28.89 |
| 50 wt % Sodium hydroxide (NaOH) dissolved in water | 5 drops |

TABLE 5B

Results

| | Selectivity (in wt. %) | Weight percentage in the effluent (wt %) |
| --- | --- | --- |
| Conversion | >99% | |
| Ethylene glycol | 50 | 4.9 |
| Propylene glycol | 17 | 1.7 |
| Butylene glycol | 1.1 | 0.10 |
| Sorbitol | 11 | 1.1 |

Example 4 and 5 illustrate that the homogeneous catalyst comprising tungsten may advantageously be recycled from the second reactor to the first reactor.

The invention claimed is:

1. A process for the production of ethylene glycol including the steps of:
   (i) providing, to a first reactor, a carbohydrate source, a solvent, hydrogen, a first heterogeneous catalyst, which first heterogeneous catalyst contains one or more transition metals from groups 8, 9 and 10 of the Periodic Table of the Elements, and a homogeneous catalyst, which homogeneous catalyst contains tungsten;
   (ii) reacting, in the first reactor, at a temperature in the range from equal to or more than 170° C. to equal to or less than 270° C., at least a portion of the carbohydrate source in the presence of the hydrogen, the solvent, the first heterogeneous catalyst and the homogeneous catalyst;
   (iii) removing, from the first reactor, a first reactor product stream and separating from such first reactor product stream at least:
   one ethylene glycol-rich fraction; and
   one sorbitol-rich fraction containing concentrated homogeneous catalyst;
   (iv) providing, to a second reactor, hydrogen and at least part of the sorbitol-rich fraction, containing concentrated homogeneous catalyst;
   (v) reacting, in the second reactor, at a temperature in the range from equal to or more than 200° C. to equal to or less than 300° C., at least a part of the sorbitol-rich fraction, containing concentrated homogeneous catalyst, in the presence of the hydrogen, a second heterogeneous catalyst, which second heterogeneous catalyst contains one or more transition metals from groups 8, 9 and 10 of the Periodic Table of the Elements;
   (vi) removing, from the second reactor, a second reactor product stream.

2. The process according to claim 1, further comprising recycling at least a portion of the second reactor product stream to the first reactor.

3. The process according to claim 1, further comprising recycling at least a portion of the homogeneous catalyst from the second reactor back to the first reactor.

4. The process according to claim 1, wherein the first reactor is a continuously stirred tank reactor.

5. The process according to claim 1, wherein the second reactor is a plug flow reactor.

6. The process according to claim 1, wherein in step (i) the carbohydrate source is provided to the first reactor by a feed stream containing the carbohydrate source and water, wherein such feed stream contains in the range from equal to or more than 2.0 wt. % to equal to or less than 50.0 wt. % of carbohydrate source, based on the total weight of the carbohydrate source and water.

7. The process according to claim 1, wherein the homogeneous catalyst contains a tungsten compound or tungsten derived from a tungsten compound, wherein such tungsten compound is sodium tungstate and/or tungstic acid and/or tungsten bronze.

8. The process according to claim 1, wherein the first heterogeneous catalyst contains ruthenium and/or nickel supported on activated carbon and/or wherein the second heterogeneous catalyst contains ruthenium and/or nickel supported on activated carbon.

9. The process according to claim 1, wherein at least a portion of the first heterogeneous catalyst and/or at least a portion of the second heterogeneous catalyst contains tungsten in addition to the one or more transition metals from groups 8, 9 and 10 of the Periodic Table of the Elements.

10. The process according to claim 1, wherein the concentration of homogeneous catalyst in the reaction mixture in the second reactor of step (v) is higher than the concentration of homogeneous catalyst in the reaction mixture in the first reactor of step (ii).

11. The process according to claim 1, wherein the concentration of homogeneous catalyst in the reaction mixture in the first reactor of step (ii) ranges from equal to or more than 0.01 wt. % to equal to or less than 0.5 wt. % of tungsten, calculated as tungsten metal, based on the total weight of the reaction mixture.

12. The process according to claim 1, wherein the one sorbitol-rich fraction containing concentrated homogeneous catalyst in step (iii) contains a concentration of homogeneous catalyst in the range from equal to or more than 0.5 wt. % to equal to or less than 10.0 wt. %, calculated as tungsten metal, based on the total weight of the sorbitol-rich fraction.

13. The process according to claim 1, wherein the concentration of homogeneous catalyst in the reaction mixture in the second reactor of step (v) ranges from equal to or more than 0.5 wt. % to equal to or less than 5 wt. %, of tungsten, calculated as tungsten metal, based on the total weight of the reaction mixture.

14. The process according to claim 1, wherein the temperature T2 during the reaction in the second reactor in step (v) is equal to or more than the temperature T1 during the reaction in the first reactor in step (ii).

15. The process according to claim 1, wherein step (iv) further comprises providing, to the second reactor, an additional solvent.

* * * * *